(12) United States Patent
Zhao et al.

(10) Patent No.: US 10,755,147 B2
(45) Date of Patent: *Aug. 25, 2020

(54) CLASSIFICATION AND LOCALIZATION BASED ON ANNOTATION INFORMATION

(71) Applicant: General Electric Company, Schenectady, NY (US)

(72) Inventors: Qian Zhao, Dublin, CA (US); Min Zhang, San Ramon, CA (US); Gopal Avinash, San Ramon, CA (US)

(73) Assignee: General Electric Company, Schenectady, NY (US)

( * ) Notice: Subject to any disclaimer, the term of this patent is extended or adjusted under 35 U.S.C. 154(b) by 117 days.

This patent is subject to a terminal disclaimer.

(21) Appl. No.: 16/046,084

(22) Filed: Jul. 26, 2018

(65) Prior Publication Data

US 2020/0012895 A1 Jan. 9, 2020

Related U.S. Application Data

(60) Provisional application No. 62/693,772, filed on Jul. 3, 2018.

(51) Int. Cl.
*G06K 9/62* (2006.01)

(52) U.S. Cl.
CPC ......... *G06K 9/6262* (2013.01); *G06K 9/6269* (2013.01); *G06K 9/6278* (2013.01); *G06K 2209/05* (2013.01)

(58) Field of Classification Search
CPC .. G06K 9/6267; G06K 9/6232; G06K 9/6215; G06K 2209/05; G06K 9/627;

(Continued)

(56) References Cited

U.S. PATENT DOCUMENTS 10,140,544 B1 * 11/2018 Zhao ................... G06K 9/3233
10,185,891 B1 * 1/2019 Martin ................. G06K 9/6218
(Continued)

OTHER PUBLICATIONS

He Kaiming et al: "Mask R-CNN", 2017 IEEE International Conference on Computer Vision (ICCV), IEEE, Oct. 22, 2017 (Oct. 22, 2017), pp. 2980-2988, XP033283165, DOI: 10.1109/ICCV.2017.322 [retrieved on Dec. 22, 2017]; abstract, p. 2961-p. 2964, figures 3-4.

(Continued)

*Primary Examiner* — Nimesh Patel
(74) *Attorney, Agent, or Firm* — Amin, Turocy & Watson, LLP

(57) ABSTRACT

Systems and techniques for classification and localization based on annotation information are presented. In one example, a system trains a convolutional neural network based on training data and a plurality of images. The training data is associated with a plurality of patients from at least one imaging device. The plurality of images is associated with a plurality of masks from a plurality of objects. The convolutional neural network comprises a decoder consisting of at least one up-sampling layer and at least one convolutional layer. The system also generates a loss function based on the plurality of masks, where the loss function is iteratively back propagated to tune parameters of the convolutional neural network. The system also predicts a classification label for an input image based on the convolutional neural network.

15 Claims, 10 Drawing Sheets

(58) Field of Classification Search
CPC ......... G06K 9/00201; G06K 2209/01; G06K 9/00281; G06K 9/3233; G06K 9/3241; G06K 9/4604; G06K 2209/051; G06K 2209/057; G06K 9/6212; G06K 9/00288; G06K 2009/3291; G06K 2209/055; G06K 9/00147; G06K 9/00248; G06K 9/00362; G06K 9/00536; G06K 9/4609; G06K 9/4619; G06K 9/6209; G06K 9/6292; G06K 9/00671; G06K 9/6262; G06K 9/66; G06K 9/6269; G06N 20/00; G06N 3/084; G06N 5/046; G06N 3/0454; G06N 3/08; G06N 3/04; G06N 3/0445; G06N 7/005; G06N 5/022; G06N 3/02; G06N 3/006; G06N 3/126; G06N 3/049; G06N 5/045; G06N 3/0427; G06N 3/082; G06N 3/0481; G06N 3/086; G06N 5/00; G06F 17/11; G06F 19/321; G06F 3/048; G06F 3/04842; G06F 9/30014; G06F 2203/011; G06F 3/013; G06F 16/3329; G06F 9/3848; G06T 7/0012; G06T 2207/20081; G06T 2207/20084; G06T 7/11; G06T 2207/10081; G06T 2207/10088; G06T 2207/10104; G06T 2207/10132; G06T 2207/10116; G06T 2207/30004; G06T 2207/30061; G06T 11/003; G06T 7/0016; G06T 2200/24; G06T 19/20; G06T 2207/20076; G06T 2207/30201; G06T 5/00; G06T 1/0007; G06T 2207/10048; G06T 7/00; G06T 7/12; G06T 7/194; G06T 7/246; G06T 11/00; G06T 13/40; G06T 19/00; G06T 3/4046; G06T 7/10; G06T 7/80; G06T 2200/04; G06T 2200/08; G06T 2207/10136; G06T 7/174; G06T 7/187; G06T 1/20; G06T 2207/10028; G06T 2207/20021; G06T 2207/20208; G06T 2207/20212; G06T 2207/20228; G06T 3/0093; G06T 3/20; G06T 3/4038; G06T 5/008; G06T 5/009; G06T 9/002; A61B 8/5223; A61B 5/0022; A61B 6/463; A61B 5/002; A61B 5/055; A61B 2034/102; A61B 2034/104; A61B 2034/105; A61B 2090/365; A61B 5/4836; A61B 5/7267; A61B 5/0037; A61B 5/7264; A61B 5/7275; A61B 5/743; A61B 5/7485; A61B 8/085; A61B 8/483; A61B 8/5207; G16H 30/40; G16H 50/20; G16H 50/50; G16H 10/60; G16H 40/63; G16H 50/30; G16H 30/20; G16H 10/00; H04L 67/12; H04L 1/18; H04L 63/1416; H04L 43/028; H04L 67/04; H04L 67/10

See application file for complete search history.

(56) References Cited

U.S. PATENT DOCUMENTS

| | | | |
|---|---|---|---|
| 2017/0169567 | A1 | 6/2017 | Chefd'Hotel et al. |
| 2017/0278289 | A1* | 9/2017 | Marino ............... G06T 7/44 |
| 2018/0075343 | A1* | 3/2018 | van den Oord ..... G06F 17/2818 |
| 2018/0082172 | A1* | 3/2018 | Patel ............... G06N 3/0472 |
| 2018/0101957 | A1* | 4/2018 | Talathi ............. G06T 3/4053 |
| 2018/0144193 | A1* | 5/2018 | Tang ............... G06K 9/00677 |
| 2018/0260957 | A1* | 9/2018 | Yang ............... G06T 7/0012 |
| 2018/0268737 | A1* | 9/2018 | Garnavi ............. G09B 7/06 |
| 2019/0043003 | A1* | 2/2019 | Fisher ............. G06K 9/6274 |
| 2019/0050981 | A1 | 2/2019 | Song et al. |
| 2019/0073569 | A1 | 3/2019 | Ben-Ari et al. |
| 2019/0122075 | A1* | 4/2019 | Zhang ............. G06T 7/0012 |
| 2019/0164290 | A1 | 5/2019 | Wang et al. |
| 2019/0205606 | A1 | 7/2019 | Zhao et al. |
| 2019/0251398 | A1* | 8/2019 | Godwin, IV ......... G06N 3/0436 |
| 2019/0286880 | A1 | 9/2019 | Jackson et al. |
| 2019/0304092 | A1 | 10/2019 | Akselrod-Ballin et al. |
| 2019/0313963 | A1* | 10/2019 | Hillen ............... G06N 20/00 |
| 2019/0318822 | A1 | 10/2019 | Zhang et al. |
| 2020/0012895 | A1* | 1/2020 | Zhao ............... G06K 9/6278 |
| 2020/0012904 | A1 | 1/2020 | Zhao et al. |

OTHER PUBLICATIONS

International Search Report/Written Opinion dated Sep. 23, 2019; pct application PCT/US2019/039711 filed Jun. 28, 2019.

Shaoqing Ren et al: "Faster R-CNN: Towards Real-Time Object Detection with Region Proposal Networks", Advances in Neural Information Processing Systems (NIPS 2015), Dec. 7, 2015 (Dec. 7, 2015), XP055488147, abstract, p. 1-p. 5, figure 1.

Zhuotun Zhu et al: "A 3D Coarse-to-Fine Framework for Automatic Pancreas Segmentation", arxiv. org, Cornell University Library, 201 Olin Library Cornell University Ithaca, NY 14853, Dec. 1, 2017 (Dec. 1, 2017), XP080843765, abstract; p. 1-p. 4, figures 1,3.

Li et al. "Thoracic Disease Identification and Localization with Limited Supervision," arXiv:1711.06373v4 [cs.CV], Mar. 28, 2018, 12 pages.

Non-Final Office Action received for U.S. Appl. No. 16/054,373 dated Mar. 25, 2020, 46 pages.

Fu et al., Joint Optic Disc and Cup Segmentation Based on Multi-Label Deep Network and Polar Transformation, Jan. 9, 2018 (first public dissemination), publish Jul. 2018 [retrivd Mar. 18, 2020], IEEE Trans on Med Imag, vol. 37, Iss: 7, pp. 1597-1605. https://ieeexplore.ieee.org/abstract/document/8252743 (Year: 2018).

Non-Final Office Action received for U.S. Appl. No. 16/058,984 dated Jan. 17, 2020, 49 pages.

Non-Final Office Action received for U.S. Appl. No. 16/143,703 dated Mar. 31, 2020, 27 pages.

PCT application PCT/US2019/039718 filed Jun. 28, 2019; International Search Report—Written Opinion dated Sep. 23, 2019, 15 pages.

* cited by examiner

CLASSIFICATION AND LOCALIZATION BASED ON ANNOTATION INFORMATION

RELATED APPLICATION

This application claims priority to U.S. Provisional Application No. 62/693,772, filed Jul. 3, 2018, and entitled "CLASSIFICATION AND/OR LOCALIZATION BASED ON ANNOTATION INFORMATION", the entirety of which is incorporated herein by reference.

TECHNICAL FIELD

This disclosure relates generally to artificial intelligence.

BACKGROUND

Artificial Intelligence (AI) can be employed for classification and/or analysis of digital images. For instance, AI can be employed for image recognition. In certain technical applications, AI can be employed to enhance imaging analysis. In an example, region-of-interest based deep neural networks can be employed to localize a feature in a digital image. However, accuracy and/or efficiency of a classification and/or an analysis of digital images using conventional artificial techniques is generally difficult to achieve. Furthermore, conventional artificial techniques for classification and/or analysis of digital images generally requires labor-intensive processes such as, for example, pixel annotations, voxel level annotations, etc. As such, conventional artificial techniques for classification and/or analysis of digital images can be improved.

SUMMARY

The following presents a simplified summary of the specification in order to provide a basic understanding of some aspects of the specification. This summary is not an extensive overview of the specification. It is intended to neither identify key or critical elements of the specification, nor delineate any scope of the particular implementations of the specification or any scope of the claims. Its sole purpose is to present some concepts of the specification in a simplified form as a prelude to the more detailed description that is presented later.

According to an embodiment, a system includes a training component, a loss function component, and a classification component. The training component trains a convolutional neural network based on training data and a plurality of images. The training data is associated with a plurality of patients from at least one imaging device. The plurality of images is associated with a plurality of masks from a plurality of objects. The convolutional neural network comprises a decoder consisting of at least one up-sampling layer and at least one convolutional layer. The loss function component generates a loss function based on the plurality of masks, where the loss function is iteratively back propagated to tune parameters of the convolutional neural network. The classification component that predicts a classification label for an input image based on the convolutional neural network.

According to another embodiment, a method is provided. The method comprises receiving a plurality of images associated with a plurality of patients from at least one imaging device. The method also comprises receiving a plurality of masks from a plurality of objects, wherein each image comprises at least one mask associating an object of interest with a corresponding class label. Furthermore, the method comprises training a convolutional neural network based on the plurality of images and the plurality of masks, where the convolutional neural network comprises a decoder consisting of at least one up-sampling layer and at least one convolutional layer, a pretrained classifier network that outputs convolutional feature maps, and a classification/localization network that outputs corresponding scoring maps. The method also comprises generating a loss function based on the plurality of masks. Additionally, the method comprises iteratively back propagating the loss function to tune parameters of the convolutional neural network. The method also comprises predicting a classification label for an input image based on the convolutional neural network.

According to yet another embodiment, a computer readable storage device is provided. The computer readable storage device comprises instructions that, in response to execution, cause a system comprising a processor to perform operations, comprising receiving a plurality of images associated with a plurality of patients from at least one imaging device. The processor also performs operations, comprising receiving a plurality of masks from a plurality of objects, where each image comprises at least one mask associating an object of interest with a corresponding class label. The processor also performs operations, comprising training a convolutional neural network based on the plurality of images and the plurality of masks, where the convolutional neural network comprises a decoder consisting of at least one up-sampling layer and at least one convolutional layer, a pretrained classifier network that outputs convolutional feature maps, and a classification/localization network that outputs corresponding scoring maps. Furthermore, the processor performs operations, comprising generating a loss function based on the plurality of masks. The processor also performs operations, comprising iteratively back propagating the loss function to tune parameters of the convolutional neural network. The processor also performs operations, comprising predicting a classification label for an input image based on the convolutional neural network.

The following description and the annexed drawings set forth certain illustrative aspects of the specification. These aspects are indicative, however, of but a few of the various ways in which the principles of the specification may be employed. Other advantages and novel features of the specification will become apparent from the following detailed description of the specification when considered in conjunction with the drawings.

BRIEF DESCRIPTION OF THE DRAWINGS

Numerous aspects, implementations, objects and advantages of the present invention will be apparent upon consideration of the following detailed description, taken in conjunction with the accompanying drawings, in which like reference characters refer to like parts throughout, and in which.

DETAILED DESCRIPTION

Figure 1:
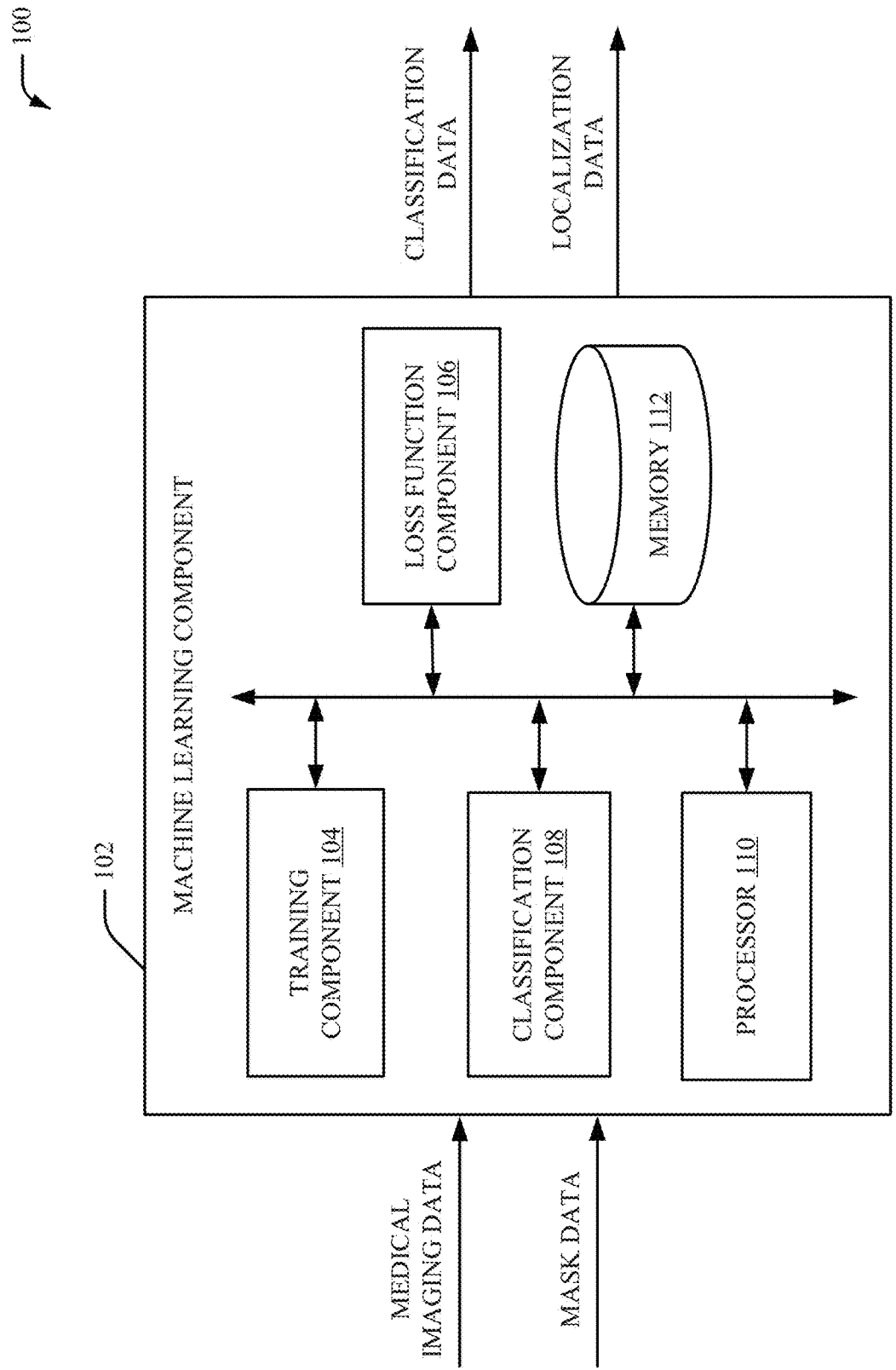
FIG. 1 illustrates a high-level block diagram of an example machine learning component, in accordance with various aspects and implementations described herein.

Various aspects of this disclosure are now described with reference to the drawings, wherein like reference numerals are used to refer to like elements throughout. In the following description, for purposes of explanation, numerous specific details are set forth in order to provide a thorough understanding of one or more aspects. It should be understood, however, that certain aspects of this disclosure may be practiced without these specific details, or with other methods, components, materials, etc. In other instances, well-known structures and devices are shown in block diagram form to facilitate describing one or more aspects.

Systems and techniques that provide classification and localization based on annotation information are presented. For instance, a novel end-to-end deep learning framework is disclosed herein to, for example, automatically detect and/or localize a disease in medical images given mask annotations pertaining to regions of interest. The classification and localization network can be a fully convolutional neural network and can output the image-level label and localization map during inference. As such, classification and/or localization accuracy while using mask information can be improved, as compared to conventional classification using image-level labels only. In an embodiment, a decoder associated with upsampling and/or a convolutional neural network layer can be employed by the end-to-end deep learning framework to, for example, improve location results. Moreover, by employing the novel end-to-end deep learning framework as described herein, detection and/or localization of one or more features associated with image data (e.g., detection and/or localization of one or more conditions for a patient associated with medical imaging data) can be improved. Furthermore, accuracy and/or efficiency for classification and/or analysis of image data (e.g., medical imaging data) can be improved. Additionally, effectiveness of a machine learning model for classification and/or analysis of image data (e.g., medical imaging data) can be improved, performance of one or more processors that execute a machine learning model for classification and/or analysis of image data (e.g., medical imaging data) can be improved, and/or efficiency of one or more processors that execute a machine learning model for classification and/or analysis of image data (e.g., medical imaging data) can be improved.

Referring initially to FIG. 1, there is illustrated an example system 100 for classification and/or localization based on annotation information, according to an aspect of the subject disclosure. The system 100 can be employed by various systems, such as, but not limited to medical device systems, medical imaging systems, medical diagnostic systems, medical systems, medical modeling systems, enterprise imaging solution systems, advanced diagnostic tool systems, simulation systems, image management platform systems, care delivery management systems, artificial intelligence systems, machine learning systems, neural network systems, modeling systems, aviation systems, power systems, distributed power systems, energy management systems, thermal management systems, transportation systems, oil and gas systems, mechanical systems, machine systems, device systems, cloud-based systems, heating systems, HVAC systems, medical systems, automobile systems, aircraft systems, water craft systems, water filtration systems, cooling systems, pump systems, engine systems, prognostics systems, machine design systems, and the like. In one example, the system 100 can be associated with a classification system to facilitate visualization and/or interpretation of medical imaging data. Moreover, the system 100 and/or the components of the system 100 can be employed to use hardware and/or software to solve problems that are highly technical in nature (e.g., related to processing digital data, related to processing medical imaging data, related to medical modeling, related to medical imaging, related to artificial intelligence, etc.), that are not abstract and that cannot be performed as a set of mental acts by a human.

The system 100 can include a machine learning component 102 that can include a training component 104, a loss function component 106, and a classification component 108. Aspects of the systems, apparatuses or processes explained in this disclosure can constitute machine-executable component(s) embodied within machine(s), e.g., embodied in one or more computer readable mediums (or media) associated with one or more machines. Such component(s), when executed by the one or more machines, e.g., computer(s), computing device(s), virtual machine(s), etc. can cause the machine(s) to perform the operations described. The system 100 (e.g., the machine learning component 102) can include memory 112 for storing computer executable components and instructions. The system 100 (e.g., the machine learning component 102) can further include a processor 110 to facilitate operation of the instructions (e.g., computer executable components and instructions) by the system 100 (e.g., the machine learning component 102).

The machine learning component 102 (e.g., the training component 104) can receive medical imaging data (e.g., MEDICAL IMAGING DATA shown in FIG. 1). The medical imaging data can be associated with the plurality of patients. Furthermore, the medical imaging data can be a set of images (e.g., a set of medical images). The medical imaging data can be two-dimensional medical imaging data and/or three-dimensional medical imaging data generated by one or more medical imaging devices. For instance, the medical imaging data can be electromagnetic radiation imagery captured via a set of sensors (e.g., a set of sensors associated with a medical imaging device). In certain embodiments, the medical imaging data can be a series of electromagnetic radiation imagery captured via a set of sensors (e.g., a set of sensors associated with a medical imaging device) during an interval of time. The medical imaging data can be received directly from one or more medical imaging devices. Alternatively, the medical imaging data can be stored in one or more databases that receives and/or stores the medical imaging data associated with the one or more medical imaging devices. A medical imaging device can be, for example, an x-ray device, a computed tomography (CT) device, another type of medical imaging device, etc. Additionally or alternatively, the machine learning component 102 (e.g., the training component 104) can receive mask data (e.g., MASK DATA shown in FIG. 1). In an embodiment, the mask data can be a set of masks from a plurality of objects. For example, each medical image from the medical imaging data can be associated with one or more masks. A mask can be a filter to mask one or more regions in an image (e.g., in the medical imaging data). For instance, a mask can include one or more weights for one or more regions of interest in an image (e.g., in the medical imaging data). In one example, a mask can include a set of pixels that define a location for region of interests using binary filtering. In an embodiment, the medical imaging data and/or the mask data can be employed as training data to, for example, train a convolutional neural network. In certain embodiments, the medical imaging data and/or the mask data can be stored in a database that receives and/or stores training data associated with the at least one imaging device. In certain embodiments, the medical imaging data can be associated with a set of weights from a pre-trained model.

In an embodiment, the training component 104 can train a convolutional neural network based on the medical imaging data (e.g., a plurality of images) and/or the mask data. For instance, the training component 104 can perform a training phase for a machine learning process to, for example, train a neural network model for the convolutional neural network. The convolutional neural network can include a decoder consisting of at least one up-sampling layer and/or at least one convolutional layer. Additionally, in certain embodiments, the convolutional neural network can include a pretrained classifier network that outputs convolutional feature maps. Additionally or alternatively, in certain embodiments, the convolutional neural network can include a classification/localization network that outputs corresponding scoring maps. In certain embodiments, the convolutional neural network can be a spring network of convolutional layers. For instance, the convolutional neural network can perform a plurality of sequential and/or parallel downsampling and upsampling of the medical imaging data associated with convolutional layers of the convolutional neural network. In an example, the convolutional neural network can perform a first convolutional layer process associated with sequential downsampling of the medical imaging data and a second convolutional layer process associated with sequential upsampling of the medical imaging data. The spring network of convolutional layers can include the first convolutional layer process associated with the sequential downsampling and the second convolutional layer process associated with sequential upsampling. The spring network of convolutional layers associated with the convolutional neural network can alter convolutional layer filters similar to functionality of a spring. For instance, the convolutional neural network can analyze the medical imaging data based on a first convolutional layer filter that comprises a first size, a second convolutional layer filter that comprises a second size that is different than the first size, and a third convolutional layer filter that comprises the first size associated with the first convolutional layer filter. In certain embodiments, the training component 104 can train the convolutional neural network based on the medical imaging data and/or the mask data (e.g., the training data) to determine whether a first class exists in the medical imaging data. Additionally or alternatively, the training component 104 can train the convolutional neural network based on the medical imaging data and/or the mask data (e.g., the training data) to form at least a portion of the convolutional neural network associated with a neural network architecture. The neural network architecture can be, for example, a binary neural network architecture that performs machine learning associated with one or more binary classifications for the medical imaging data.

The loss function component 106 can generate a loss function based on the plurality of masks associated with the medical imaging data. The loss function can be, for example, a loss function for the convolutional neural network. In certain embodiments, the loss function component 106 can employ the decoder to generate a localization map. For instance, the loss function component 106 can perform a decoding process associated with upsampling and/or one or more convolutional neural network layers to generate a localization map. The localization map can include, for example, information representing a probability score for one or more regions of the medical imaging data. In an embodiment, the localization map can include a visualization representing a probability score for one or more regions of the medical imaging data. In certain embodiments, the decoder can be a set of decoders. In an aspect, the decoder can be a set of decoders that perform distinct decoding processes associated with upsampling and/or or one or more convolutional neural network layers. For instance, the decoder can include a first decoder that performs a first decoding process associated with upsampling and/or or one or more convolutional neural network layers, a second decoder that performs a second decoding process associated with upsampling and/or or one or more convolutional neural network layers, a third decoder that performs a third decoding process associated with upsampling and/or or one or more convolutional neural network layers, etc. In another aspect, a number of decoders included in the set of decoders can be determined during training of the convolutional neural network. In certain embodiments, the loss function component 106 can generate the loss function based on a probability for a class associated with the plurality of masks. For instance, the loss function component 106 can generate the loss function based on a probability associated with classification output from the convolutional neural network and the plurality of masks. In an aspect, the loss function can be iteratively back propagated to tune one or more parameters of the convolutional neural network. For example, the convolutional neural network can be modified based on the loss function to improve the classification output from the convolutional neural network.

The classification component 108 can predict a classification label for an input image based on the convolutional neural network. The convolutional neural network employed by the classification component 108 can be a version of the convolutional neural that is tuned based on the loss function. The input image can be, for example, a medical image. The input image can be a two-dimensional image (e.g., a two-dimensional medical image) and/or three-dimensional image (e.g., a three-dimensional medical image) generated by one or more medical imaging devices. For instance, the input image can be a two-dimensional image (e.g., a two-dimensional medical image) and/or three-dimensional image (e.g., a three-dimensional medical image) generated by an x-ray device, a CT device, another type of medical imaging device, etc. In one example, the input image can be an electromagnetic radiation image captured via a set of sensors (e.g., a set of sensors associated with a medical imaging device). In certain embodiments, the input image can be a series of electromagnetic radiation images captured via a set of sensors (e.g., a set of sensors associated with a medical imaging device) during an interval of time. The input image can be received directly from one or more medical imaging devices. Alternatively, the input image can be stored in one or more databases that receives and/or stores the input image associated with the one or more medical imaging devices. In an aspect, the convolutional neural network can include a classification/localization network that outputs corresponding scoring maps based on the convolutional feature maps. In another aspect, a size of a mask from the plurality of masks can be matched with a size of a convolutional feature map from the convolutional feature maps. Additionally or alternatively, a size of a mask from the plurality of masks can be matched with a size of a convolutional feature map from the convolutional feature maps based on a max pooling process.

In certain embodiments, the classification component 108 can extract information that is indicative of correlations, inferences and/or expressions from the input image based on the convolutional neural network (e.g., a version of the convolutional neural that is tuned based on the loss function). The classification component 108 can generate the learned imaging output based on the execution of at least one machine learning model associated with the convolutional neural network (e.g., a version of the convolutional neural that is tuned based on the loss function). In an aspect, the classification component 108 can generate learned imaging output. The learned imaging output generated by the classification component 108 can include, for example, learning, correlations, inferences and/or expressions associated with the input image. In an aspect, the classification component 108 can perform learning with respect to the input image explicitly or implicitly using the convolutional neural network (e.g., a version of the convolutional neural that is tuned based on the loss function). The classification component 108 can also employ an automatic classification system and/or an automatic classification process to facilitate analysis of the input image. For example, the classification component 108 can employ a probabilistic and/or statistical-based analysis (e.g., factoring into the analysis utilities and costs) to learn and/or generate inferences with respect to the input image. The classification component 108 can employ, for example, a support vector machine (SVM) classifier to learn and/or generate inferences for imaging data. Additionally or alternatively, the classification component 108 can employ other classification techniques associated with Bayesian networks, decision trees and/or probabilistic classification models. Classifiers employed by the classification component 108 can be explicitly trained (e.g., via a generic training data) as well as implicitly trained (e.g., via receiving extrinsic information). For example, with respect to SVM's, SVM's can be configured via a learning or training phase within a classifier constructor and feature selection module. A classifier can be a function that maps an input attribute vector, x=(x1, x2, x3, x4, xn), to a confidence that the input belongs to a class—that is, f(x)=confidence(class).

It is to be appreciated that technical features of the machine learning component 102 are highly technical in nature and not abstract ideas. Processing threads of the machine learning component 102 that process and/or analyze the medical imaging data, determine outlier medical imaging data, etc. cannot be performed by a human (e.g., are greater than the capability of a single human mind). For example, the amount of the medical imaging data processed, the speed of processing of the medical imaging data and/or the data types of the medical imaging data processed by the machine learning component 102 over a certain period of time can be respectively greater, faster and different than the amount, speed and data type that can be processed by a single human mind over the same period of time. Furthermore, the medical imaging data processed by the machine learning component 102 can be one or more medical images generated by sensors of a medical imaging device. Moreover, the machine learning component 102 can be fully operational towards performing one or more other functions (e.g., fully powered on, fully executed, etc.) while also processing the medical imaging data.

Figure 2:
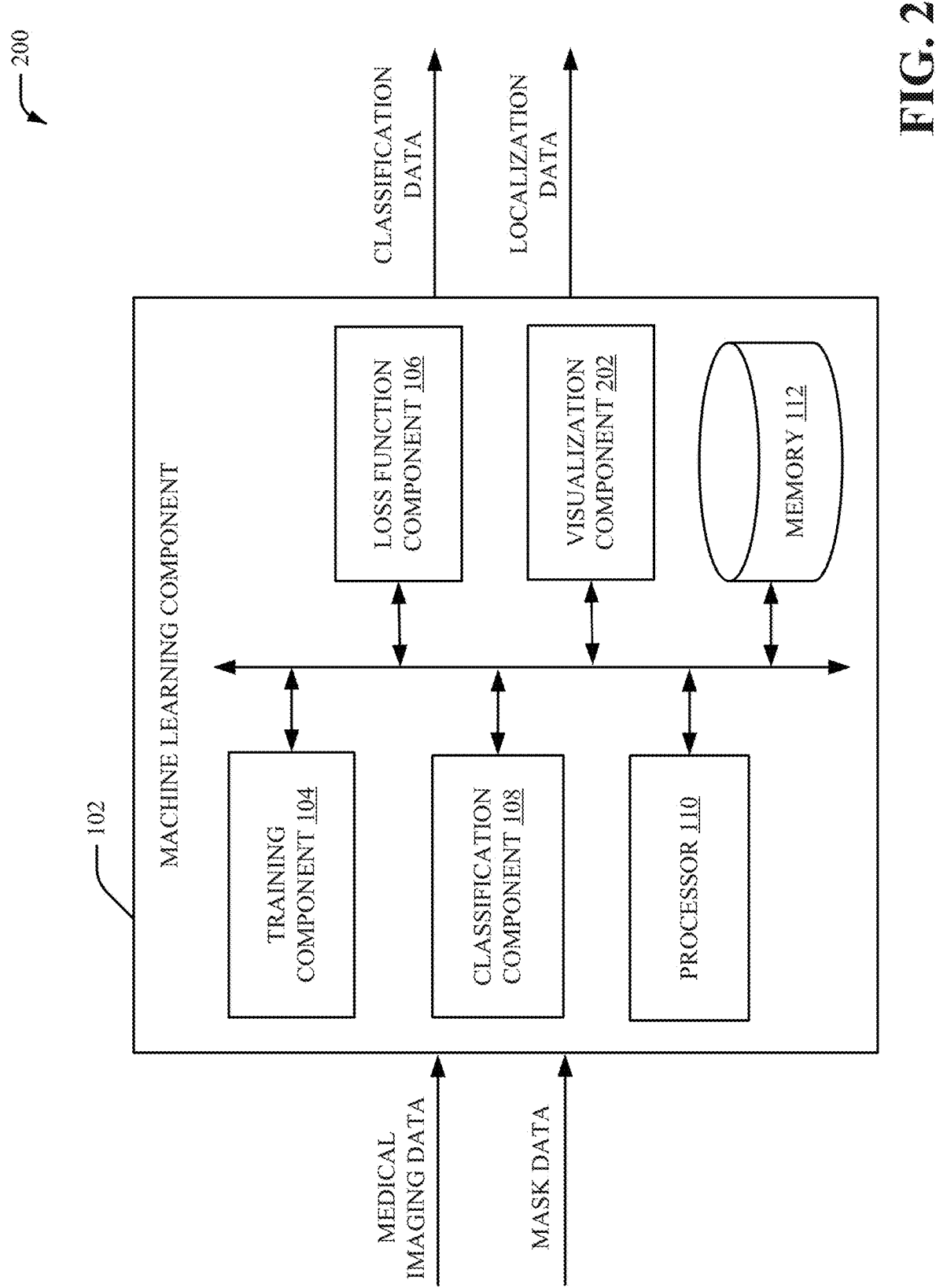
FIG. 2 illustrates a high-level block diagram of another example machine learning component, in accordance with various aspects and implementations described herein.

Referring now to FIG. 2, there is illustrated a non-limiting implementation of a system 200 in accordance with various aspects and implementations of this disclosure. Repetitive description of like elements employed in other embodiments described herein is omitted for sake of brevity.

The system 200 includes the machine learning component 102. The machine learning component 102 can include the training component 104, the loss function component 106, the classification component 108, a visualization component 202, the processor 110 and/or the memory 112. The visualization component 202 can generate a multi-dimensional visualization associated with the classification label for the input image classified by the classification component 108. Additionally or alternatively, the visualization component 202 can generate a multi-dimensional visualization associated with localization information for the input image classified by the classification component 108. For instance, the visualization component 202 can generate a human-interpretable visualization of the classification label for the input image and/or the localization information for the input image. Additionally or alternatively, visualization component 202 can generate a human-interpretable visualization of the input image and/or the medical imaging data. In an embodiment, the visualization component 202 can generate deep learning data based on a classification and/or a localization for a portion of an anatomical region associated with the input image. The deep learning data can include, for example, a classification and/or a location for one or more diseases located in the input image. In certain embodiments, the deep learning data can include probability data indicative of a probability for one or more diseases being located in the input image. The probability data can be, for example, a probability array of data values for one or more diseases being located in the input image. Additionally or alternatively, the visualization component 202 can generate a multi-dimensional visualization associated with classification and/or localization for a portion of an anatomical region associated with the input image.

The multi-dimensional visualization can be a graphical representation of the input image that shows a classification and/or a location of one or more diseases with respect to a patient body. The visualization component 202 can also generate a display of the multi-dimensional visualization of the diagnosis provided by a medical imaging diagnosis process. For example, the visualization component 202 can render a 2D visualization of a portion of an anatomical region on a user interface associated with a display of a user device such as, but not limited to, a computing device, a computer, a desktop computer, a laptop computer, a monitor device, a smart device, a smart phone, a mobile device, a handheld device, a tablet, a portable computing device or another type of user device associated with a display. In an aspect, the multi-dimensional visualization can include deep learning data. In another aspect, the deep learning data can also be rendered on the 3D model as one or more dynamic visual elements. The visualization component 202 can, in an embodiment, alter visual characteristics (e.g., color, size, hues, shading, etc.) of at least a portion of the deep learning data associated with the multi-dimensional visualization based on the classification and/or the localization for the portion of the anatomical region. For example, the classification and/or the localization for the portion of the anatomical region can be presented as different visual characteristics (e.g., colors, sizes, hues or shades, etc.), based on a result of deep learning and/or medical imaging diagnosis. In another aspect, the visualization component 202 can allow a user to zoom into or out with respect to the deep learning data associated with the multi-dimensional visualization. For example, the visualization component 202 can allow a user to zoom into or out with respect to a classification and/or a location of one or more diseases identified in the anatomical region of the patient body. As such, a user can view, analyze and/or interact with the deep learning data associated with the multi-dimensional visualization for the input image.

Figure 3:
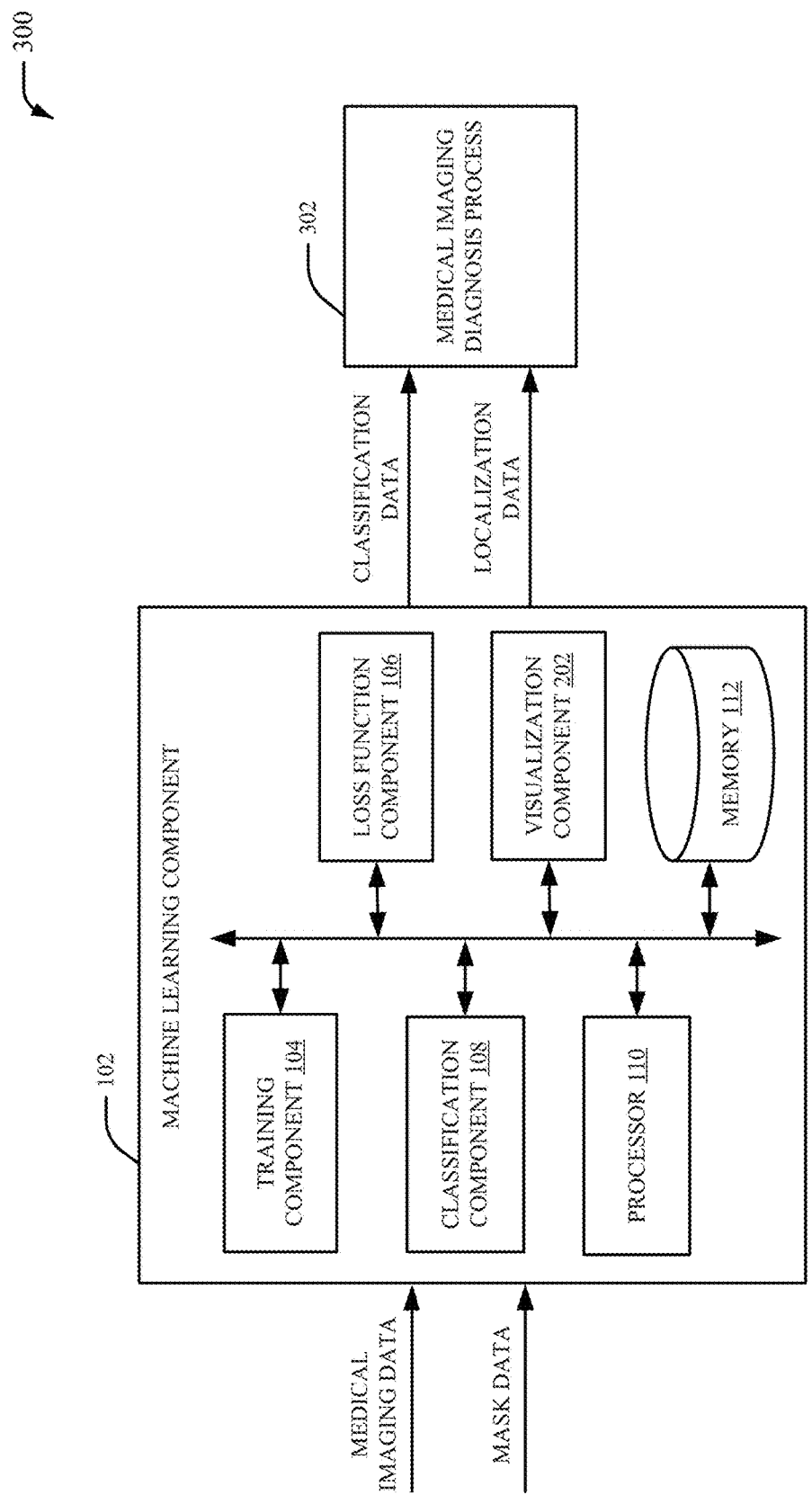
FIG. 3 illustrates a system that includes an example machine learning component and an example medical imaging diagnosis process, in accordance with various aspects and implementations described herein.

Referring now to FIG. 3, there is illustrated a non-limiting implementation of a system 300 in accordance with various aspects and implementations of this disclosure. Repetitive description of like elements employed in other embodiments described herein is omitted for sake of brevity.

The system 300 includes the machine learning component 102 and medical imaging diagnosis process 302. The machine learning component 102 can provide the classification data and/or the localization data to the medical imaging diagnosis process 302. The classification data and/or the localization data can include one or more classifications and/or localization information associated with the input image. In an aspect, the classification data and/or the localization data can be generated by the classification component 108. In an embodiment, the medical imaging diagnosis process 302 can perform deep learning to facilitate classification and/or localization of one or more diseases associated with the input image and/or the medical imaging data. In another aspect, the medical imaging diagnosis process 302 can perform deep learning based on a convolutional neural network that receives the input image and/or the medical imaging data. A disease classified and/or localized by the medical imaging diagnosis process 302 can include, for example, a lung disease, a heart disease, a tissue disease, a bone disease, a tumor, a cancer, tuberculosis, cardiomegaly, hypoinflation of a lung, opacity of a lung, hyperdistension, a spine degenerative disease, calcinosis, or another type of disease associated with an anatomical region of a patient body. In an aspect, the medical imaging diagnosis process 302 can determine a prediction for a disease associated with the input image and/or the medical imaging data. For example, the medical imaging diagnosis process 302 can determine a probability score for a disease associated with the input image and/or the medical imaging data (e.g., a first percentage value representing likelihood of a negative prognosis for the disease and a second value representing a likelihood of a positive prognosis for the disease).

Figure 4:
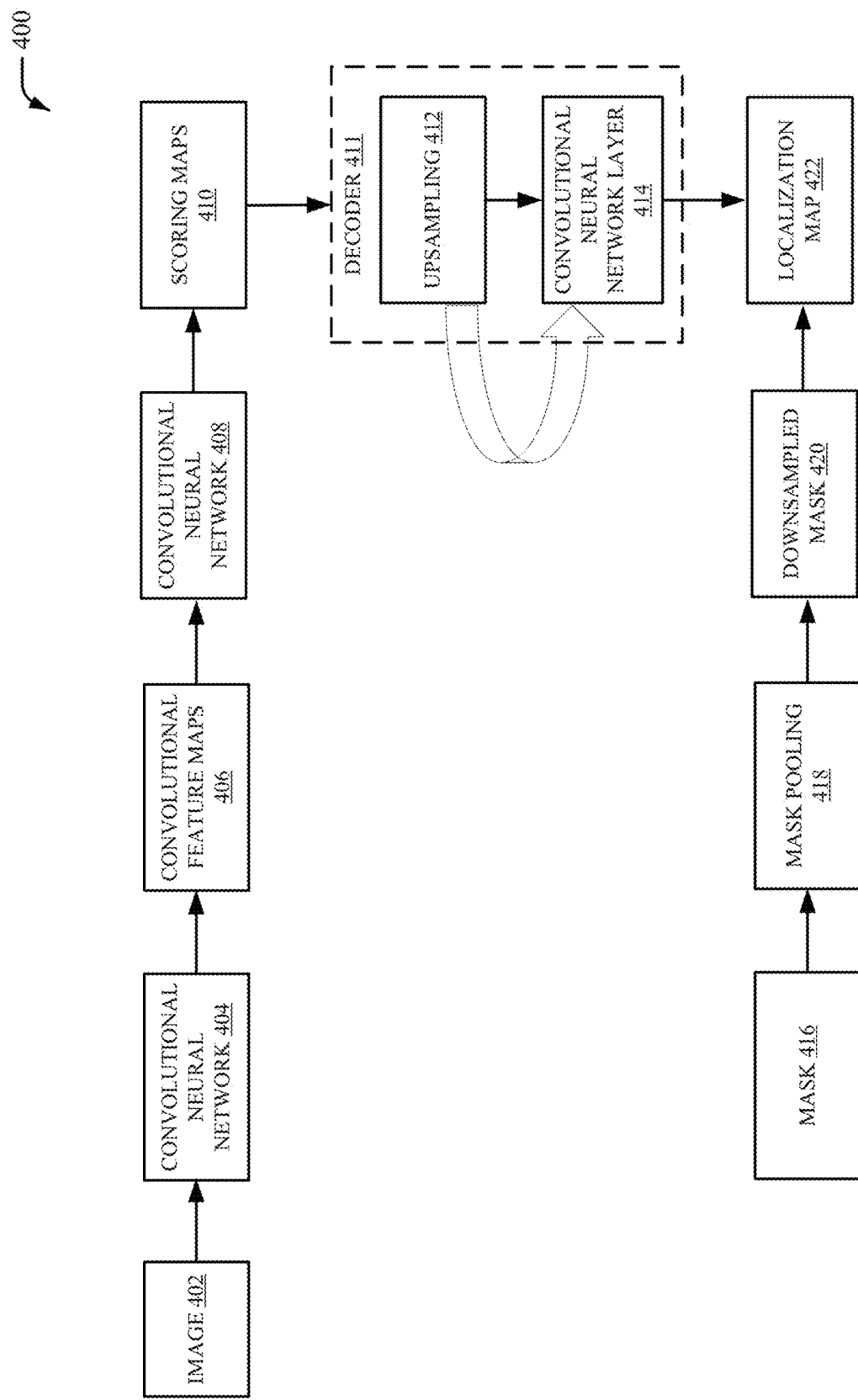
FIG. 4 illustrates another example system associated with a segmentation-classification network, in accordance with various aspects and implementations described herein.

Referring now to FIG. 4, there is illustrated a non-limiting implementation of a system 400 in accordance with various aspects and implementations of this disclosure. Repetitive description of like elements employed in other embodiments described herein is omitted for sake of brevity.

The system 400 can be a classification-localization network. In an embodiment, the system 400 can represent a machine learning process and/or another process performed by the machine learning component 102 (e.g., the training component 104, the loss function component 106, the classification component 108, and/or the visualization component 202). An image 402 (e.g., an input image) can be processed by a convolutional neural network 404. The image 402 can be, for example, a medical image. For instance, the image 402 can be a two-dimensional image (e.g., a two-dimensional medical image) and/or three-dimensional image (e.g., a three-dimensional medical image) generated by one or more medical imaging devices. In one example, the image 402 can be a two-dimensional image (e.g., a two-dimensional medical image) and/or three-dimensional image (e.g., a three-dimensional medical image) generated by an x-ray device, a CT device, another type of medical imaging device, etc. In another example, the image 402 can be an electromagnetic radiation image captured via a set of sensors (e.g., a set of sensors associated with a medical imaging device). In certain embodiments, the image 402 can be a series of electromagnetic radiation images captured via a set of sensors (e.g., a set of sensors associated with a medical imaging device) during an interval of time. The image 402 can be received directly from one or more medical imaging devices. Alternatively, the image 402 can be stored in one or more databases that receives and/or stores the image 402 associated with the one or more medical imaging devices. In an embodiment, the image 402 can be an input image analyzed by the machine learning component 102 (e.g., an input image classified by the classification component 108).

The convolutional neural network 404 can output convolutional feature maps 406, which can be employed by a convolutional neural network 408 (e.g., a classification and localization network) that creates scoring maps 410. In an aspect, the convolutional neural network 404 can encode the image 402 into the convolutional feature maps 406. In an embodiment, the convolutional neural network 404 can be a spring network of convolutional layers. For instance, the convolutional neural network can perform a plurality of sequential and/or parallel downsampling and ups ampling of the image 402 associated with convolutional layers of the convolutional neural network 404 to generate the convolutional feature maps 406. In an example, the convolutional neural network 404 can perform a first convolutional layer process associated with sequential downsampling of the image 402 and a second convolutional layer process associated with sequential upsampling of the image 402 to generate the convolutional feature maps 406. The spring network of convolutional layers can include the first convolutional layer process associated with the sequential downsampling and the second convolutional layer process associated with sequential upsampling. The spring network of convolutional layers associated with the convolutional neural network can alter convolutional layer filters similar to functionality of a spring. For instance, the convolutional neural network 404 can analyze the image 402 based on a first convolutional layer filter that comprises a first size, a second convolutional layer filter that comprises a second size that is different than the first size, and a third convolutional layer filter that comprises the first size associated with the first convolutional layer filter to generate the convolutional feature maps 406. The convolutional feature maps 406 can be, for example, data that represent output of convolutional layer filters applied to a previous convolutional layer. For example, a first convolutional feature map from the convolutional feature maps 406 can include first data that represents output of a first convolutional layer filter applied to a previous convolutional layer, a second convolutional feature map from the convolutional feature maps 406 can include second data that represents output of a second convolutional layer filter applied to a previous convolutional layer, a third convolutional feature map from the convolutional feature maps 406 can include third data that represents output of a third convolutional layer filter applied to a previous convolutional layer, etc. In another embodiment, the convolutional neural network 408 can be a 1×1 convolutional layer that generates the scoring maps 410 based on the convolutional feature maps 406. The scoring maps 410 can include prediction scores for a class associated with regions of interest for the image 402.

In an aspect, during training of the convolutional neural network 404, a mask 416 of the image 402 can be matched with a size of the convolutional feature maps 406 via mask pooling 418. For instance, the mask pooling 418 can compare the mask 516 (e.g., the predicted mask) with the downsampled mask 420 (e.g., the downsampled ground truth mask). A size of the downsampled mask 420 can, for example correspond to a size of the mask 416. In one example, during training of the convolutional neural network 404, the mask 416 can be a mask of a region of interest for the image 402 that is matched with a size of at least one convolutional feature map from the convolutional feature maps 406. Furthermore, the mask pooling 418 can perform rational mask pooling to compare the mask 416 (e.g., the predicted mask) with the downsampled mask 420 (e.g., the downsampled ground truth mask) of the same size. In an embodiment, a class label for the image 402 can be implicit and can be determined based on the mask 416. For example, a mask element associated with the mask 416 that is above a defined threshold can signal presence of a class. For testing, the scoring maps 410 can provide a predicted classification label with a localization map 422. The localization map 422 can include, for example, information representing a probability score for one or more regions of the image 402. In certain embodiments, the localization map 422 can include a visualization representing a probability score for one or more regions of the image 402.

The system 400 can also include a decoder 411. The decoder 411 can include upsampling 412 and/or a convolutional neural network layer 414. In an aspect, the decoder 411 can be implemented as a repeatable segmentation network where the upsampling 412 and the convolutional neural network layer 414 can be repeated blocks a certain number of times. In another aspect, the decoder 411 can generate the localization map 422. For instance, the decoder 411 can perform a decoding process associated with the upsampling 412 and/or the convolutional neural network layer 414 to generate the localization map 422. The decoder 411 can provide improved localization results associated with the image 402. In an embodiment, a number of decoder blocks associated with the decoder 411 can be treated as a hyperparameter during training of the convolutional neural network 404. In another embodiment, the upsampling 412 can perform bilinear interpolation to upsample the scoring maps 412 to a certain size. In yet another embodiment, the convolutional neural network layer 414 can be configured as a recognition network that includes a set of filters, a batch normalization process and/or a set of rectified linear units to generate a set of predictions for the localization map 422. The decoder 411 can also provide smoother and more accurate heat maps in a final classification and/or localization result for the image 402. In another aspect, the system 400 can provide improved the performance of a classifier based on the mask 416 pertaining to regions of interest and/or image level labels for the image 402.

Figure 5:
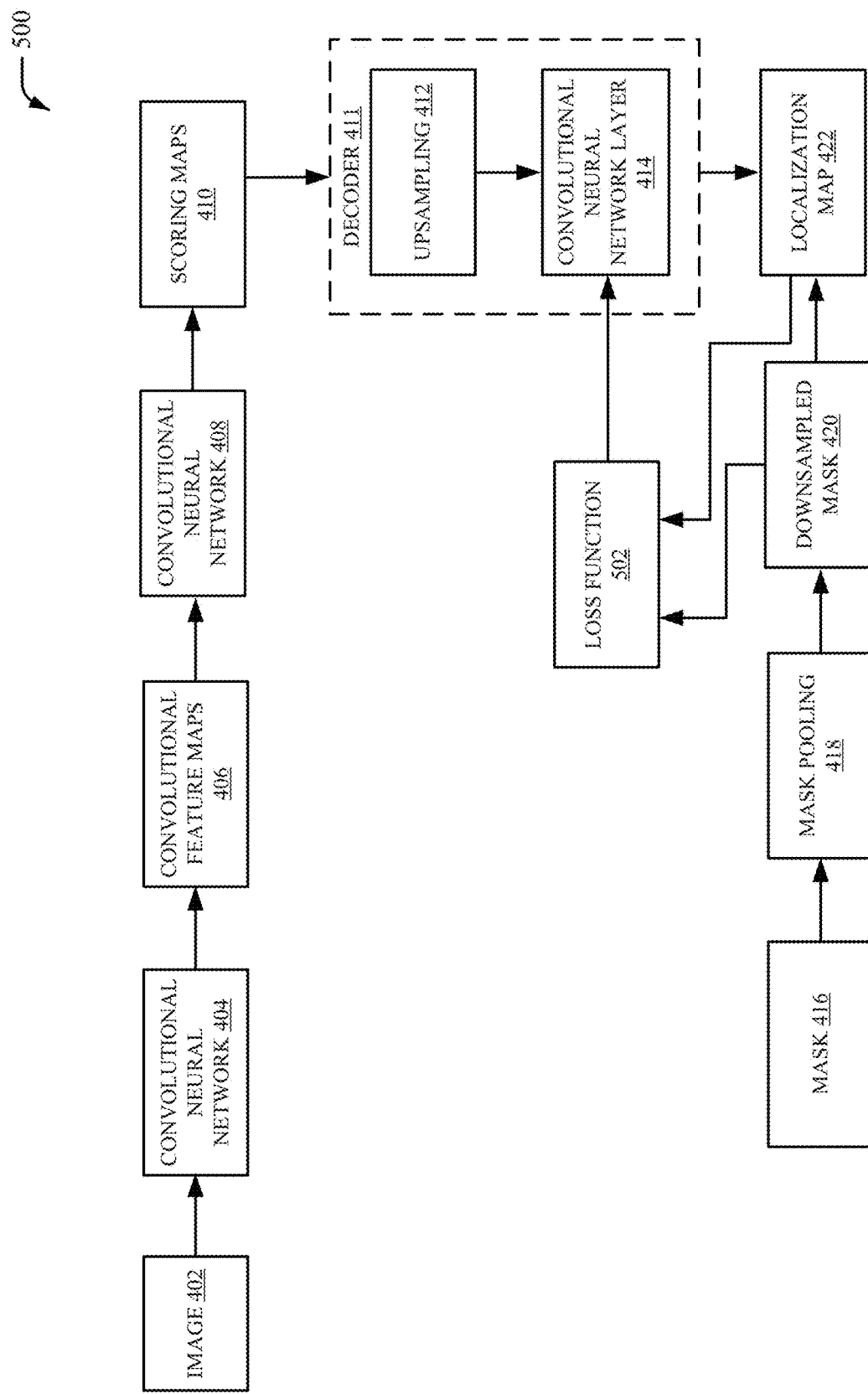
FIG. 5 illustrates another example system associated with a segmentation-classification network implementing a loss function, in accordance with various aspects and implementations described herein.

Referring now to FIG. 5, there is illustrated a non-limiting implementation of a system 500 in accordance with various aspects and implementations of this disclosure. Repetitive description of like elements employed in other embodiments described herein is omitted for sake of brevity.

The system 500 can be a classification-localization network that includes a loss function 502. In an embodiment, the system 500 can represent a machine learning process and/or another process performed by the machine learning component 102 (e.g., the training component 104, the loss function component 106, the classification component 108, and/or the visualization component 202). The system 500 can include the image 402, the convolutional neural network 404, the convolutional feature maps 406, the convolutional neural network 408, the scoring maps 410, and the decoder 411 that includes the upsampling 412 and the convolutional neural network layer 414. The system 500 can also include the mask 416, the mask pooling 418, the downsampled mask 420, the localization map 422 and the loss function 502. The loss function 502 can be a loss function that is created based on the downsampled mask 420 (e.g., the downsampled ground truth mask) and the mask 416 (e.g., the predicted mask) during training of the convolutional neural network 404. The loss function can, for example, be represented by the following equation:

$$\text{Loss}_{mask} = -\Sigma_i \log(p(y_k|x_i,\text{mask}_i^k))$$

where $p(y_k|x_i,\text{mask}_i^k)$ is a probability of an image i being positive for class k with respect to a total area in image i and/or a region covered by a mask. Furthermore, $y_k$ can be a kth output from the convolutional neural network 404 that denotes whether the image i is positive for class k, where $x_i$ is an ith image. In an embodiment, the loss function 502 can be generated based on the downsampled mask 420 and/or the localization map 422. For instance, the loss function 502 can be generated based on a probability for a class associated with the downsampled mask 420 and/or the localization map 422. Furthermore, the loss function 502 can be provided to the convolutional neural network layer 414. Additionally, the loss function 502 can be back propagated from the convolutional neural network layer 414 to the convolutional neural network 404. For instance, the loss function 502 can be back propagated through the system 500 starting from the convolutional neural network layer 414 and ending at the convolutional neural network 404. In an aspect, the loss function 502 can tune one or more parameters of the convolutional neural network 404. For example, the convolutional neural network 404 can be modified based on the loss function 502 to improve classification and/or localization results associated with the localization map 422.

Figure 6:
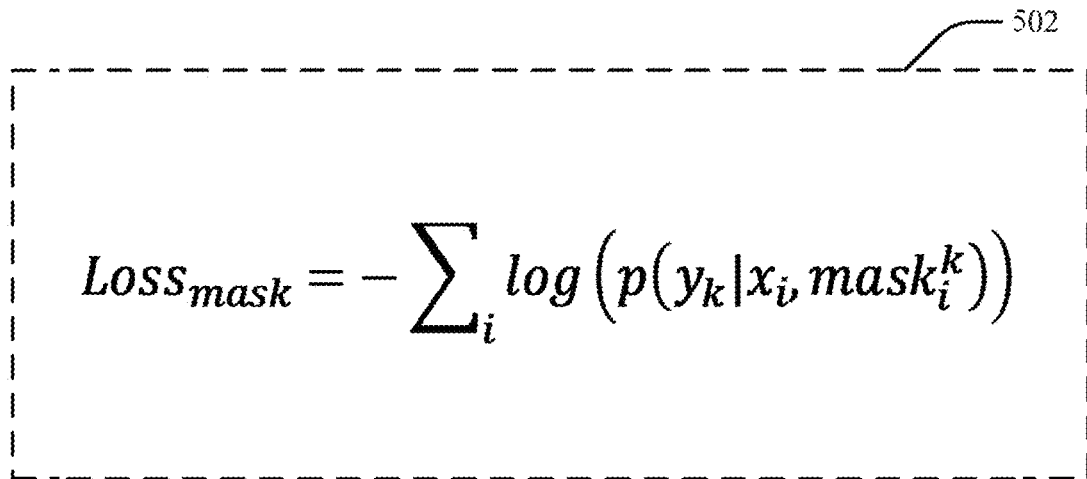
FIG. 6 illustrates an example loss function, in accordance with various aspects and implementations described herein.

Referring now to FIG. 6, there is illustrated a non-limiting example of the loss function 502 in accordance with various aspects and implementations of this disclosure. Repetitive description of like elements employed in other embodiments described herein is omitted for sake of brevity.

As discussed above, the loss function 502 can be represented by the following equation:

$$\text{Loss}_{mask} = -\Sigma_i \log(p(y_k|x_i,\text{mask}_i^k))$$

For instance, the loss function 502 can be generated based on a probability for a class associated with the downsampled mask 420 and/or the mask 416. By employing the loss function 502 and/or annotation information (e.g. the mask 416 and/or the downsampled mask 420), classification accuracy can be improved. The system 400 and/or the system 500 can also output improved localization maps (e.g., more accurate localization maps). For example, the loss function 502 and/or annotation information (e.g. the mask 416 and/or the downsampled mask 420) can be employed to provide improved localization information associated with the localization map 422.

In a non-limiting embodiment that employs the system 400 and/or the system 500, experiments on a dataset can consist of medical condition and non-medical condition X-ray images that are extracted from a database. A medical condition can include, for example, a lung disease, a heart disease, a tissue disease, a bone disease, a tumor, a cancer, tuberculosis, cardiomegaly, hypoinflation of a lung, opacity of a lung, hyperdistension, a spine degenerative disease, calcinosis, pneumothorax, or another type of medical condition associated with an anatomical region of a patient body. The medical condition masks can be annotated, for example, by radiologists. A total of 1806 images can be split to 1444 images for training (e.g., 80% of the images), 180 images for validation (e.g., 10% of the images) and 182 images for testing (10% of the images), as shown below in Table I. Experimental results are shown below in Table II. Testing accuracy of the system 400 and/or the system 500 is 0.923 and AUC is 0.979 with dice coefficient 0.5, which outperforms a conventional classification network trained only with image-level labels.

TABLE I

Description of medical condition dataset

| Dataset | Training (80%) | Validation (10%) | Testing (10%) |
|---|---|---|---|
| Medical Condition | 722 | 90 | 91 |
| Non-Medical Condition | 722 | 90 | 91 |
| Total | 1444 | 180 | 182 |

TABLE II

Experimental Results

| Model | val Accuracy | val Precision | val Recall | val AUC | val Dice | test Accuracy | test Precision | test Recall | test AUC |
|---|---|---|---|---|---|---|---|---|---|
| Conventional Classification Network | 0.894 | 0.899 | 0.889 | 0.941 | | 0.896 | 0.875 | 0.923 | 0.945 |
| System 400 and/or System 500 | 0.95 | 0.966 | 0.933 | 0.98 | 0.518 | 0.923 | 0.953 | 0.89 | 0.979 |

According, as seen from experimental results in Table II, by providing richer annotation information (e.g. masks), classification accuracy can be improved and a convolutional neural network can also output improved localization maps (e.g., more accurate localization maps). This can be achieved by the same underlying prediction model for both tasks. The system 400 and/or the system 500 can also be flexible and can be generalized to other applications due to a selectable convolutional neural network framework associated with the system 400 and/or the system 500, a repeatable segmentation network associated with the system 400 and/or the system 500, and a tunable mask size associated with the system 400 and/or the system 500. As such, the system 400 and/or the system 500 can jointly model classification and/or localization. Furthermore, the system 400 and/or the system 500 can apply the classification and/or the localization to disease detection (e.g., medical condition detection, etc.) in medical imaging data (e.g., X-ray images) and/or other digital images.

Figure 7:
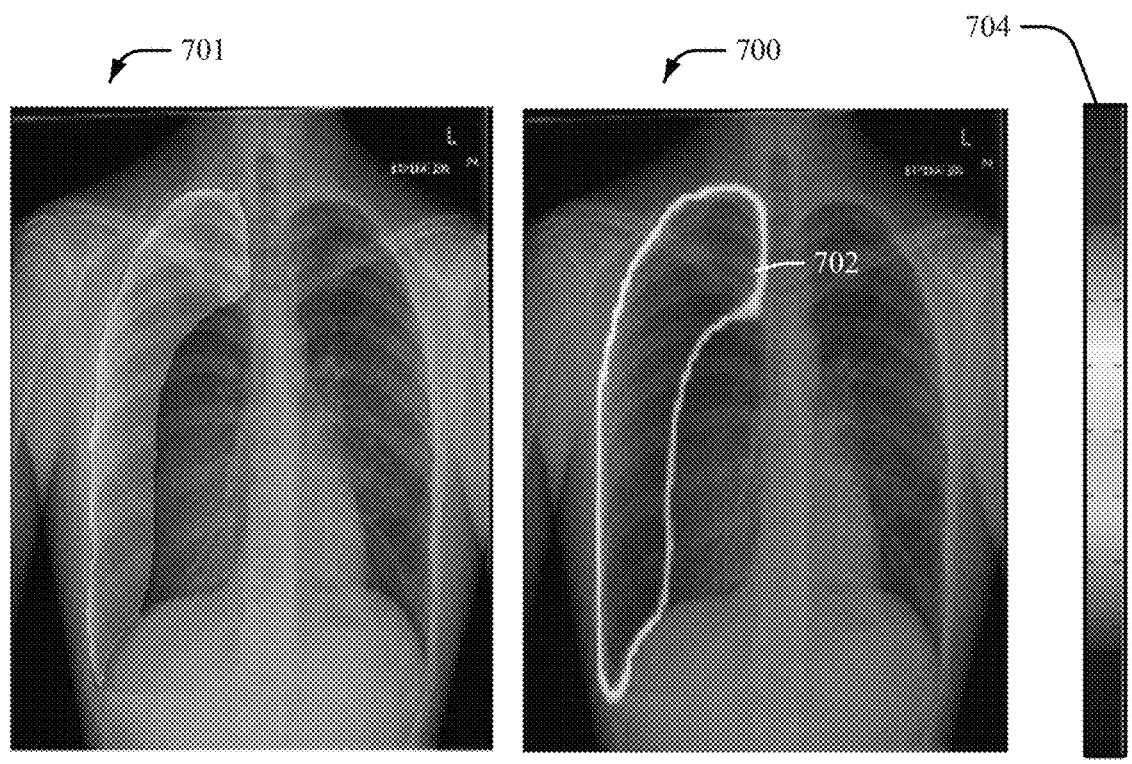
FIG. 7 illustrates another example multi-dimensional visualization, in accordance with various aspects and implementations described herein.

FIG. 7 illustrates an example multi-dimensional visualization 700 and an example input image 701, in accordance with various aspects and implementations described herein. In the embodiment shown in FIG. 7, the multi-dimensional visualization 700 can, for example, display a medical imaging diagnosis for a patient. For example, the multi-dimensional visualization 700 can display one or more classifications and/or one or more localizations for one or more conditions identified in imaging data (e.g., the input image 701). However, it is to be appreciated that the multi-dimensional visualization 700 can be associated with another type of classification and/or location for one or more features located in imaging data. In an aspect, the multi-dimensional visualization 700 can include localization data 702 for a medical imaging diagnosis. The localization data 702 can be a predicted location for a condition associated with the input image and/or the medical imaging data processed by the machine learning component 102. Visual characteristics (e.g., a color, a size, hues, shading, etc.) of the localization data 702 can be dynamic based on information provided by the machine learning component 102. For instance, a first portion of the localization data 702 can comprise a first visual characteristic, a second portion of the localization data 702 can comprise a second visual characteristic, a third portion of the localization data 702 can comprise a third visual characteristic, etc. In an embodiment, a display environment associated with the multi-dimensional visualization 700 can include a heat bar 704. The heat bar 704 can include a set of colors that correspond to different values for the localization data 702. For example, a first color (e.g., a color red) in the heat bar 704 can correspond to a first value for the localization data 702, a second color (e.g., a color green) in the heat bar 704 can correspond to a second value for the localization data 702, a third color (e.g., a color blue) in the heat bar 704 can correspond to a third value for the localization data 702, etc.

Figure 8:
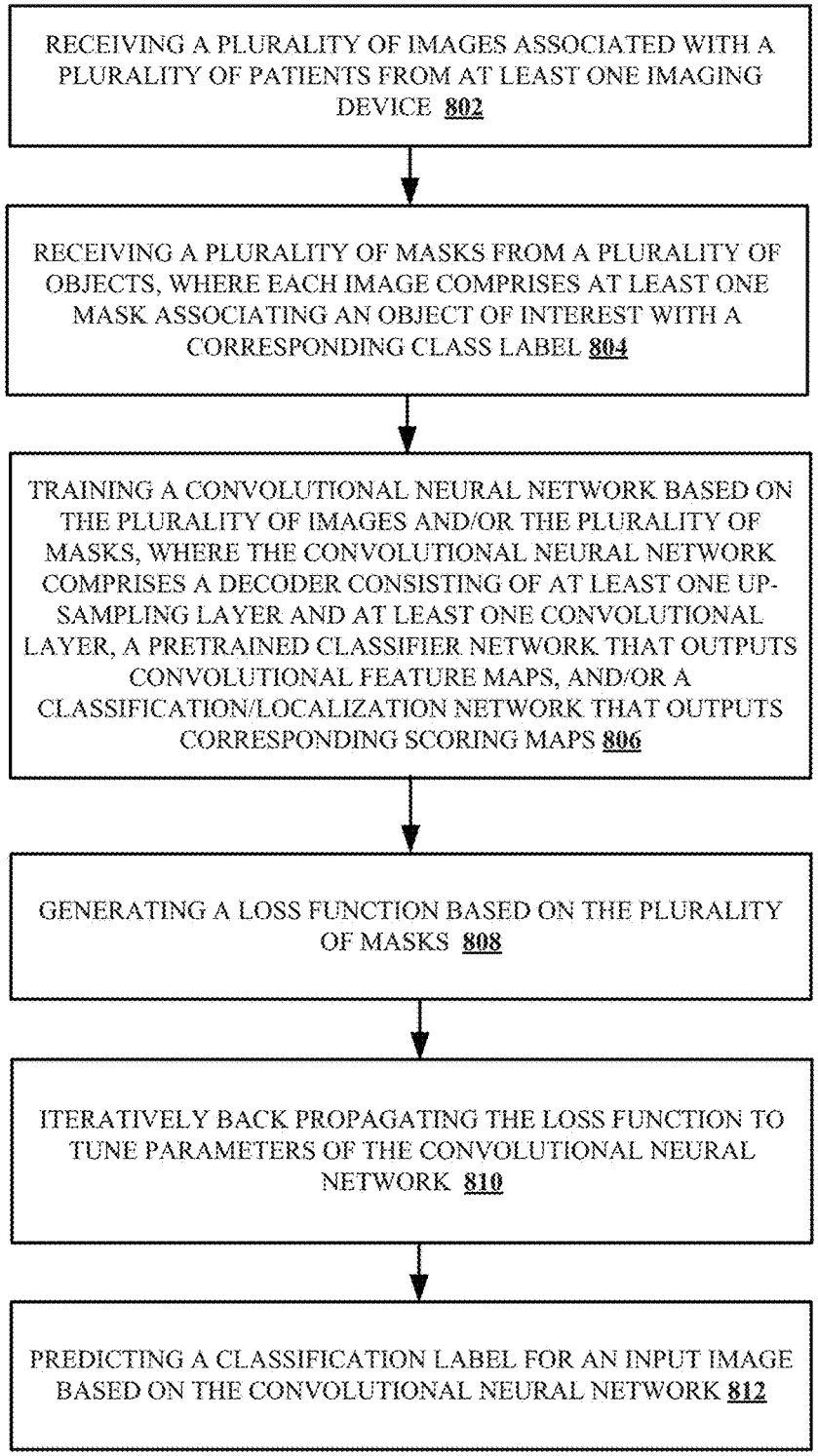
FIG. 8 depicts a flow diagram of another example method for classification and/or localization based on annotation information, in accordance with various aspects and implementations described herein.

FIG. 8 illustrates a methodology and/or a flow diagram in accordance with the disclosed subject matter. For simplicity of explanation, the methodology is depicted and described as a series of acts. It is to be understood and appreciated that the subject innovation is not limited by the acts illustrated and/or by the order of acts, for example acts can occur in various orders and/or concurrently, and with other acts not presented and described herein. Furthermore, not all illustrated acts may be required to implement the methodology in accordance with the disclosed subject matter. In addition, those skilled in the art will understand and appreciate that the methodology could alternatively be represented as a series of interrelated states via a state diagram or events. Additionally, it should be further appreciated that methodologies disclosed hereinafter and throughout this specification are capable of being stored on an article of manufacture to facilitate transporting and transferring such methodologies to computers. The term article of manufacture, as used herein, is intended to encompass a computer program accessible from any computer-readable device or storage media.

Referring to FIG. 8, there is illustrated a non-limiting implementation of a methodology 800 for classification and/or localization based on annotation information, according to an aspect of the subject innovation. At 802, a plurality of images associated with a plurality of patients is received (e.g., by training component 104) from at least one imaging device. The plurality of images can be associated with the plurality of patients. Furthermore, the plurality of images can be a set of medical images. The plurality of images can be two-dimensional images and/or three-dimensional images generated by one or more medical imaging devices. For instance, the plurality of images can be electromagnetic radiation imagery captured via a set of sensors (e.g., a set of sensors associated with a medical imaging device). In certain embodiments, the plurality of images can be a series of electromagnetic radiation imagery captured via a set of sensors (e.g., a set of sensors associated with a medical imaging device) during an interval of time. The plurality of images can be received directly from one or more medical imaging devices. Alternatively, the plurality of images can be stored in one or more databases that receives and/or stores the plurality of images associated with the one or more medical imaging devices. A medical imaging device can be, for example, an x-ray device, a CT device, another type of medical imaging device, etc. In an embodiment, each image from the plurality of images can be associated with one or more masks.

At 804, a plurality of masks from a plurality of objects is received (e.g., by training component 104), where each image comprises at least one mask associating an object of interest with a corresponding class label. A mask can be a filter to mask one or more regions in an image (e.g., an image from the plurality of images). For instance, a mask can include one or more weights for one or more regions of interest in an image (e.g., an image from the plurality of images). In one example, a mask can include a set of pixels that define a location for region of interests using binary filtering.

At 806, a convolutional neural network is trained (e.g., by training component 104) based on the plurality of images and/or the plurality of masks, where the convolutional neural network comprises a decoder consisting of at least one up-sampling layer and at least one convolutional layer, a pretrained classifier network that outputs convolutional feature maps, and/or a classification/localization network that outputs corresponding scoring maps. The decoder can be implemented as a repeatable segmentation network where the at least one upsampling layer and/or the at least one convolutional neural network layer can be repeated blocks a certain number of times.

At 808, a loss function is generated (e.g., by loss function component 106) based on the plurality of masks. In an aspect, the loss function can be generated by employing the decoder to generate the localization map. In certain embodiments, a number of decoders associated with the decoder can be determined during training of the convolutional neural network. In another aspect, the loss function can be generated based on a probability for a class associated with the plurality of masks. In an embodiment, the loss function can be generated based on a downsampled mask (e.g., a ground truth mask) and another mask (e.g., a predicted mask) during training of the convolutional neural network. In another embodiment, the loss function can be generated based on a downsampled mask and/or the localization map. For instance, the loss function can be generated based on a probability for a class associated with the a downsampled mask and/or a mask.

At 810, the loss function is iteratively back propagated (e.g., by loss function component 106) to tune parameters of the convolutional neural network based on the training data. For example, the loss function can be provided to the at least one convolutional neural network layer for the decoder. Additionally, the loss function can be back propagated from the at least one convolutional neural network layer to the convolutional neural network to modify one or more portions of the convolutional neural network.

At 812, a classification label for an input image is predicted (e.g., by classification component 108) based on the convolutional neural network. The convolutional neural network employed to predict the classification label can be a version of the convolutional neural that is tuned based on the loss function. The image can be, for example, a medical image. The input image can be a two-dimensional image (e.g., a two-dimensional medical image) and/or three-dimensional image (e.g., a three-dimensional medical image) generated by one or more medical imaging devices. For instance, the input image can be a two-dimensional image (e.g., a two-dimensional medical image) and/or three-dimensional image (e.g., a three-dimensional medical image) generated by an x-ray device, a CT device, another type of medical imaging device, etc. In one example, the input image can be an electromagnetic radiation image captured via a set of sensors (e.g., a set of sensors associated with a medical imaging device). In certain embodiments, the input image can be a series of electromagnetic radiation images captured via a set of sensors (e.g., a set of sensors associated with a medical imaging device) during an interval of time. The input image can be received directly from one or more medical imaging devices. Alternatively, the input image can be stored in one or more databases that receives and/or stores the input image associated with the one or more medical imaging devices. In certain embodiments, the methodology 800 can further include matching a size of a mask from the plurality of masks with a size of a convolutional feature map from the convolutional feature maps. In certain embodiments, the methodology 800 can further include matching a size of a mask from the plurality of masks with a size of a convolutional feature map from the convolutional feature maps based on a max pooling process. In certain embodiments, the methodology 800 can further include generating a multi-dimensional visualization associated with the classification label for the input image. In certain embodiments, the decoder can generate a localization map. For instance, the decoder can perform a decoding process associated with the at least one ups ampling layer and/or the at least one convolutional neural network layer to generate a localization map.

The aforementioned systems and/or devices have been described with respect to interaction between several components. It should be appreciated that such systems and components can include those components or sub-components specified therein, some of the specified components or sub-components, and/or additional components. Sub-components could also be implemented as components communicatively coupled to other components rather than included within parent components. Further yet, one or more components and/or sub-components may be combined into a single component providing aggregate functionality. The components may also interact with one or more other components not specifically described herein for the sake of brevity, but known by those of skill in the art.

Figure 9:
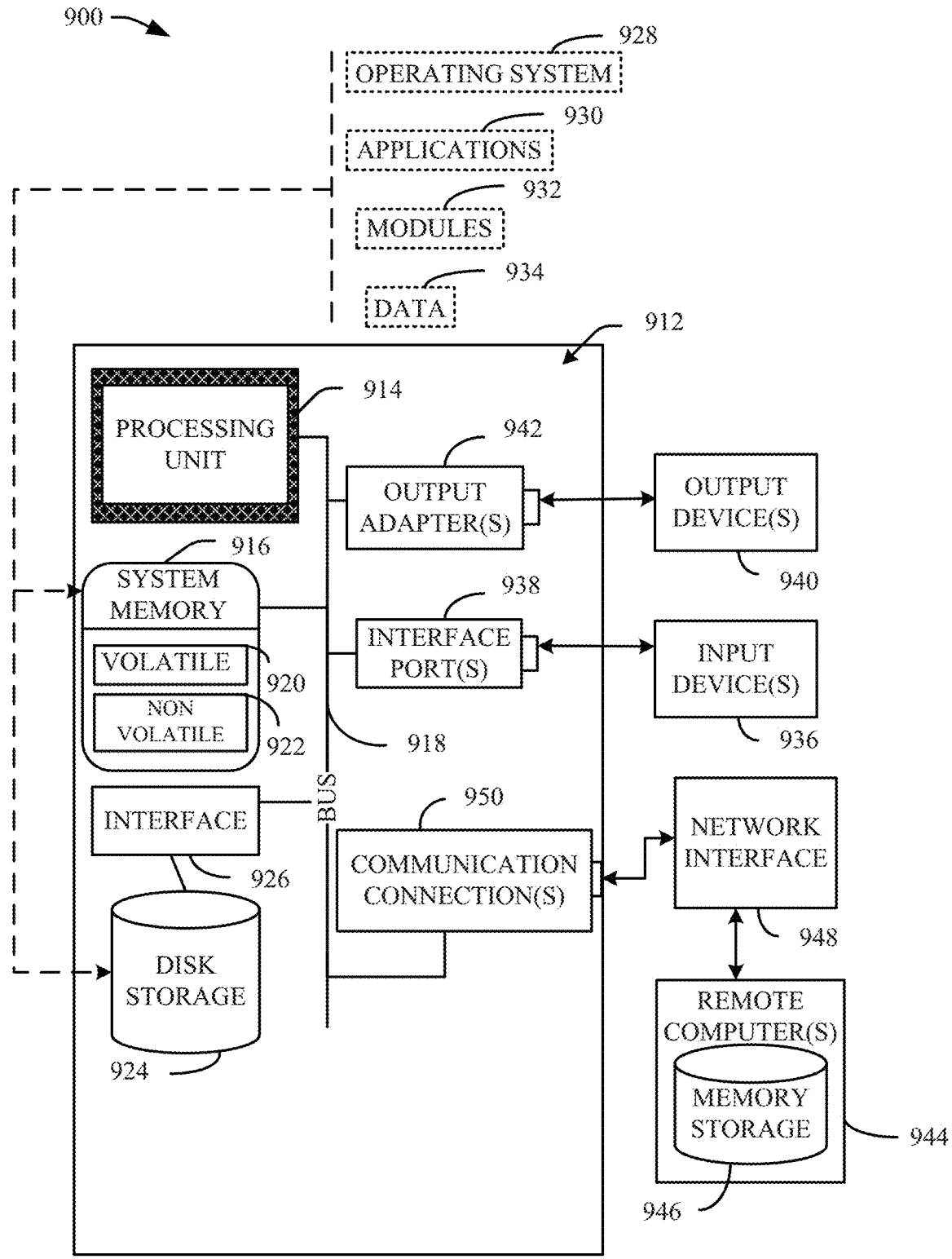
FIG. 9 is a schematic block diagram illustrating a suitable operating environment.
Figure 10:
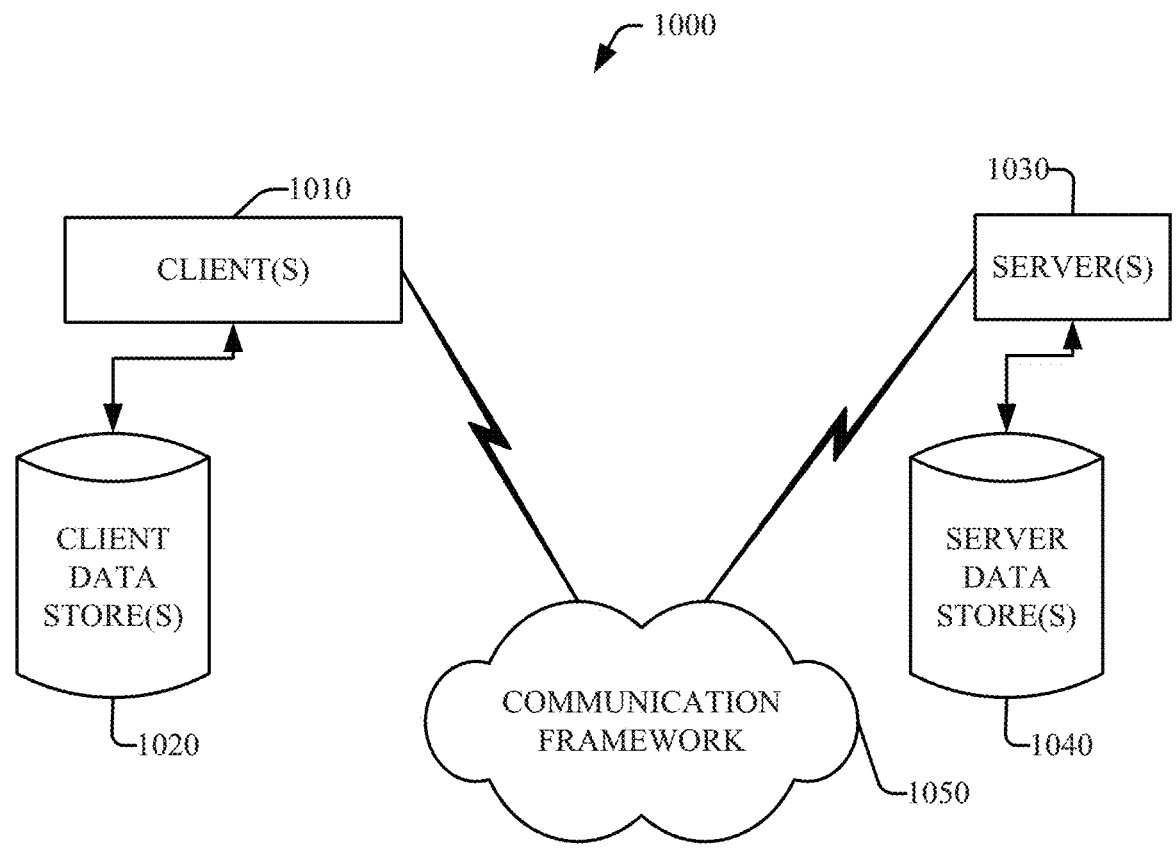
FIG. 10 is a schematic block diagram of a sample-computing environment.

In order to provide a context for the various aspects of the disclosed subject matter, FIGS. 9 and 10 as well as the following discussion are intended to provide a brief, general description of a suitable environment in which the various aspects of the disclosed subject matter may be implemented.

With reference to FIG. 9, a suitable environment 900 for implementing various aspects of this disclosure includes a computer 912. The computer 912 includes a processing unit 914, a system memory 916, and a system bus 918. The system bus 918 couples system components including, but not limited to, the system memory 916 to the processing unit 914. The processing unit 914 can be any of various available processors. Dual microprocessors and other multiprocessor architectures also can be employed as the processing unit 914.

The system bus 918 can be any of several types of bus structure(s) including the memory bus or memory controller, a peripheral bus or external bus, and/or a local bus using any variety of available bus architectures including, but not limited to, Industrial Standard Architecture (ISA), Micro-Channel Architecture (MSA), Extended ISA (EISA), Intelligent Drive Electronics (IDE), VESA Local Bus (VLB), Peripheral Component Interconnect (PCI), Card Bus, Universal Serial Bus (USB), Advanced Graphics Port (AGP), Personal Computer Memory Card International Association bus (PCMCIA), Firewire (IEEE 1394), and Small Computer Systems Interface (SCSI).

The system memory 916 includes volatile memory 920 and nonvolatile memory 922. The basic input/output system (BIOS), containing the basic routines to transfer information between elements within the computer 912, such as during start-up, is stored in nonvolatile memory 922. By way of illustration, and not limitation, nonvolatile memory 922 can include read only memory (ROM), programmable ROM (PROM), electrically programmable ROM (EPROM), electrically erasable programmable ROM (EEPROM), flash memory, or nonvolatile random access memory (RAM) (e.g., ferroelectric RAM (FeRAM). Volatile memory 920 includes random access memory (RAM), which acts as external cache memory. By way of illustration and not limitation, RAM is available in many forms such as static RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), direct Rambus RAM (DRRAM), direct Rambus dynamic RAM (DRDRAM), and Rambus dynamic RAM.

Computer 912 also includes removable/non-removable, volatile/nonvolatile computer storage media. FIG. 9 illustrates, for example, a disk storage 924. Disk storage 924 includes, but is not limited to, devices like a magnetic disk drive, floppy disk drive, tape drive, Jaz drive, Zip drive, LS-100 drive, flash memory card, or memory stick. The disk storage 924 also can include storage media separately or in combination with other storage media including, but not limited to, an optical disk drive such as a compact disk ROM device (CD-ROM), CD recordable drive (CD-R Drive), CD rewritable drive (CD-RW Drive) or a digital versatile disk ROM drive (DVD-ROM). To facilitate connection of the disk storage devices 924 to the system bus 918, a removable or non-removable interface is typically used, such as interface 926.

FIG. 9 also depicts software that acts as an intermediary between users and the basic computer resources described in the suitable operating environment 900. Such software includes, for example, an operating system 928. Operating system 928, which can be stored on disk storage 924, acts to control and allocate resources of the computer system 912. System applications 930 take advantage of the management of resources by operating system 928 through program modules 932 and program data 934, e.g., stored either in system memory 916 or on disk storage 924. It is to be appreciated that this disclosure can be implemented with various operating systems or combinations of operating systems.

A user enters commands or information into the computer 912 through input device(s) 936. Input devices 936 include, but are not limited to, a pointing device such as a mouse, trackball, stylus, touch pad, keyboard, microphone, joystick, game pad, satellite dish, scanner, TV tuner card, digital camera, digital video camera, web camera, and the like. These and other input devices connect to the processing unit 914 through the system bus 918 via interface port(s) 938. Interface port(s) 938 include, for example, a serial port, a parallel port, a game port, and a universal serial bus (USB). Output device(s) 940 use some of the same type of ports as input device(s) 936. Thus, for example, a USB port may be used to provide input to computer 912, and to output information from computer 912 to an output device 940. Output adapter 942 is provided to illustrate that there are some output devices 940 like monitors, speakers, and printers, among other output devices 940, which require special adapters. The output adapters 942 include, by way of illustration and not limitation, video and sound cards that provide a means of connection between the output device 940 and the system bus 918. It should be noted that other devices and/or systems of devices provide both input and output capabilities such as remote computer(s) 944.

Computer 912 can operate in a networked environment using logical connections to one or more remote computers, such as remote computer(s) 944. The remote computer(s) 944 can be a personal computer, a server, a router, a network PC, a workstation, a microprocessor based appliance, a peer device or other common network node and the like, and typically includes many or all of the elements described relative to computer 912. For purposes of brevity, only a memory storage device 946 is illustrated with remote computer(s) 944. Remote computer(s) 944 is logically connected to computer 912 through a network interface 948 and then physically connected via communication connection 950. Network interface 948 encompasses wire and/or wireless communication networks such as local-area networks (LAN), wide-area networks (WAN), cellular networks, etc. LAN technologies include Fiber Distributed Data Interface (FDDI), Copper Distributed Data Interface (CDDI), Ethernet, Token Ring and the like. WAN technologies include, but are not limited to, point-to-point links, circuit switching networks like Integrated Services Digital Networks (ISDN) and variations thereon, packet switching networks, and Digital Subscriber Lines (DSL).

Communication connection(s) 950 refers to the hardware/software employed to connect the network interface 948 to the bus 918. While communication connection 950 is shown for illustrative clarity inside computer 912, it can also be external to computer 912. The hardware/software necessary for connection to the network interface 948 includes, for exemplary purposes only, internal and external technologies such as, modems including regular telephone grade modems, cable modems and DSL modems, ISDN adapters, and Ethernet cards.

FIG. 10 is a schematic block diagram of a sample-computing environment 1000 with which the subject matter of this disclosure can interact. The system 1000 includes one or more client(s) 1010. The client(s) 1010 can be hardware and/or software (e.g., threads, processes, computing devices). The system 1000 also includes one or more server(s) 1030. Thus, system 1000 can correspond to a two-tier client server model or a multi-tier model (e.g., client, middle tier server, data server), amongst other models. The server(s) 1030 can also be hardware and/or software (e.g., threads, processes, computing devices). The servers 1030 can house threads to perform transformations by employing this disclosure, for example. One possible communication between a client 1010 and a server 1030 may be in the form of a data packet transmitted between two or more computer processes.

The system 1000 includes a communication framework 1050 that can be employed to facilitate communications between the client(s) 1010 and the server(s) 1030. The client(s) 1010 are operatively connected to one or more client data store(s) 1020 that can be employed to store information local to the client(s) 1010. Similarly, the server(s) 1030 are operatively connected to one or more server data store(s) 1040 that can be employed to store information local to the servers 1030.

It is to be noted that aspects or features of this disclosure can be exploited in substantially any wireless telecommunication or radio technology, e.g., Wi-Fi; Bluetooth; Worldwide Interoperability for Microwave Access (WiMAX); Enhanced General Packet Radio Service (Enhanced GPRS); Third Generation Partnership Project (3GPP) Long Term Evolution (LTE); Third Generation Partnership Project 2 (3GPP2) Ultra Mobile Broadband (UMB); 3GPP Universal Mobile Telecommunication System (UMTS); High Speed Packet Access (HSPA); High Speed Downlink Packet Access (HSDPA); High Speed Uplink Packet Access (HSUPA); GSM (Global System for Mobile Communications) EDGE (Enhanced Data Rates for GSM Evolution) Radio Access Network (GERAN); UMTS Terrestrial Radio Access Network (UTRAN); LTE Advanced (LTE-A); etc. Additionally, some or all of the aspects described herein can be exploited in legacy telecommunication technologies, e.g., GSM. In addition, mobile as well non-mobile networks (e.g., the Internet, data service network such as internet protocol television (IPTV), etc.) can exploit aspects or features described herein.

While the subject matter has been described above in the general context of computer-executable instructions of a computer program that runs on a computer and/or computers, those skilled in the art will recognize that this disclosure also can or may be implemented in combination with other program modules. Generally, program modules include routines, programs, components, data structures, etc. that perform particular tasks and/or implement particular abstract data types. Moreover, those skilled in the art will appreciate that the inventive methods may be practiced with other computer system configurations, including single-processor or multiprocessor computer systems, mini-computing devices, mainframe computers, as well as personal computers, hand-held computing devices (e.g., PDA, phone), microprocessor-based or programmable consumer or industrial electronics, and the like. The illustrated aspects may also be practiced in distributed computing environments where tasks are performed by remote processing devices that are linked through a communications network. However, some, if not all aspects of this disclosure can be practiced on stand-alone computers. In a distributed computing environment, program modules may be located in both local and remote memory storage devices.

As used in this application, the terms "component," "system," "platform," "interface," and the like, can refer to and/or can include a computer-related entity or an entity related to an operational machine with one or more specific functionalities. The entities disclosed herein can be either hardware, a combination of hardware and software, software, or software in execution. For example, a component may be, but is not limited to being, a process running on a processor, a processor, an object, an executable, a thread of execution, a program, and/or a computer. By way of illustration, both an application running on a server and the server can be a component. One or more components may reside within a process and/or thread of execution and a component may be localized on one computer and/or distributed between two or more computers.

In another example, respective components can execute from various computer readable media having various data structures stored thereon. The components may communicate via local and/or remote processes such as in accordance with a signal having one or more data packets (e.g., data from one component interacting with another component in a local system, distributed system, and/or across a network such as the Internet with other systems via the signal). As another example, a component can be an apparatus with specific functionality provided by mechanical parts operated by electric or electronic circuitry, which is operated by a software or firmware application executed by a processor. In such a case, the processor can be internal or external to the apparatus and can execute at least a part of the software or firmware application. As yet another example, a component can be an apparatus that provides specific functionality through electronic components without mechanical parts, wherein the electronic components can include a processor or other means to execute software or firmware that confers at least in part the functionality of the electronic components. In an aspect, a component can emulate an electronic component via a virtual machine, e.g., within a cloud computing system.

In addition, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. Moreover, articles "a" and "an" as used in the subject specification and annexed drawings should generally be construed to mean "one or more" unless specified otherwise or clear from context to be directed to a singular form.

As used herein, the terms "example" and/or "exemplary" are utilized to mean serving as an example, instance, or illustration. For the avoidance of doubt, the subject matter disclosed herein is not limited by such examples. In addition, any aspect or design described herein as an "example" and/or "exemplary" is not necessarily to be construed as preferred or advantageous over other aspects or designs, nor is it meant to preclude equivalent exemplary structures and techniques known to those of ordinary skill in the art.

Various aspects or features described herein can be implemented as a method, apparatus, system, or article of manufacture using standard programming or engineering techniques. In addition, various aspects or features disclosed in this disclosure can be realized through program modules that implement at least one or more of the methods disclosed herein, the program modules being stored in a memory and executed by at least a processor. Other combinations of hardware and software or hardware and firmware can enable or implement aspects described herein, including a disclosed method(s). The term "article of manufacture" as used herein can encompass a computer program accessible from any computer-readable device, carrier, or storage media. For example, computer readable storage media can include but are not limited to magnetic storage devices (e.g., hard disk, floppy disk, magnetic strips . . . ), optical discs (e.g., compact disc (CD), digital versatile disc (DVD), blu-ray disc (BD) . . . ), smart cards, and flash memory devices (e.g., card, stick, key drive . . . ), or the like.

As it is employed in the subject specification, the term "processor" can refer to substantially any computing processing unit or device comprising, but not limited to, single-core processors; single-processors with software multithread execution capability; multi-core processors; multi-core processors with software multithread execution capability; multi-core processors with hardware multithread technology; parallel platforms; and parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components, or any combination thereof designed to perform the functions described herein. Further, processors can exploit nano-scale architectures such as, but not limited to, molecular and quantum-dot based transistors, switches and gates, in order to optimize space usage or enhance performance of user equipment. A processor may also be implemented as a combination of computing processing units.

In this disclosure, terms such as "store," "storage," "data store," data storage," "database," and substantially any other information storage component relevant to operation and functionality of a component are utilized to refer to "memory components," entities embodied in a "memory," or components comprising a memory. It is to be appreciated that memory and/or memory components described herein can be either volatile memory or nonvolatile memory, or can include both volatile and nonvolatile memory.

By way of illustration, and not limitation, nonvolatile memory can include read only memory (ROM), programmable ROM (PROM), electrically programmable ROM (EPROM), electrically erasable ROM (EEPROM), flash memory, or nonvolatile random access memory (RAM) (e.g., ferroelectric RAM (FeRAM). Volatile memory can include RAM, which can act as external cache memory, for example. By way of illustration and not limitation, RAM is available in many forms such as synchronous RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), direct Rambus RAM (DRRAM), direct Rambus dynamic RAM (DRDRAM), and Rambus dynamic RAM (RDRAM). Additionally, the disclosed memory components of systems or methods herein are intended to include, without being limited to including, these and any other suitable types of memory.

It is to be appreciated and understood that components, as described with regard to a particular system or method, can include the same or similar functionality as respective components (e.g., respectively named components or similarly named components) as described with regard to other systems or methods disclosed herein.

What has been described above includes examples of systems and methods that provide advantages of this disclosure. It is, of course, not possible to describe every conceivable combination of components or methods for purposes of describing this disclosure, but one of ordinary skill in the art may recognize that many further combinations and permutations of this disclosure are possible. Furthermore, to the extent that the terms "includes," "has," "possesses," and the like are used in the detailed description, claims, appendices and drawings such terms are intended to be inclusive in a manner similar to the term "comprising" as "comprising" is interpreted when employed as a transitional word in a claim.

What is claimed is:

1. A machine learning system that employs masks and decoders for improved performance, comprising:
    a memory that stores computer executable components;
    a processor that executes computer executable components stored in the memory, wherein the computer executable components comprise:
        a training component that trains a convolutional neural network based on training data and a plurality of images, wherein the training data is associated with a plurality of patients from at least one imaging device, wherein the plurality of images is associated with a plurality of masks from a plurality of objects, and wherein the convolutional neural network comprises a decoder consisting of at least one up-sampling layer and at least one convolutional layer, wherein the decoder is a set of decoders, and wherein a number of decoders included in the set of decoders is determined during training of the convolutional neural network;
        a loss function component that generates a loss function based on the plurality of masks, wherein the loss function is iteratively back propagated to tune parameters of the convolutional neural network;
        a classification component that predicts a classification label for an input image based on the convolutional neural network; and
        a visualization component that generates a multi-dimensional visualization associated with the classification label for the input image.

2. The machine learning system of claim 1, wherein the convolutional neural network comprises a pretrained classifier network that outputs convolutional feature maps.

3. The machine learning system of claim 2, wherein the convolutional neural network comprises a classification/localization network that outputs corresponding scoring maps based on the convolutional feature maps.

4. The machine learning system of claim 2, wherein a size of a mask from the plurality of masks is matched with a size of a convolutional feature map from the convolutional feature maps.

5. The machine learning system of claim 2, wherein a size of a mask from the plurality of masks is matched with a size of a convolutional feature map from the convolutional feature maps based on a max pooling process.

6. The machine learning system of claim 1, wherein the loss function component employs the decoder to generate the localization map.

7. The machine learning system of claim 1, wherein the loss function component generates the loss function based on a probability for a class associated with the plurality of masks.

8. A method that employs masks and decoders for improved performance, comprising using a processor operatively coupled to memory to execute computer executable components to perform the following acts:

receiving a plurality of images associated with a plurality of patients from at least one imaging device;

receiving a plurality of masks from a plurality of objects, wherein each image comprises at least one mask associating an object of interest with a corresponding class label;

training a convolutional neural network based on the plurality of images and the plurality of masks, wherein the convolutional neural network comprises a decoder consisting of at least one up-sampling layer and at least one convolutional layer, a pretrained classifier network that outputs convolutional feature maps, and a classification/localization network that outputs corresponding scoring maps, wherein the decoder is a set of decoders,;

determining a number of decoders in the set of decoders during the training of the convolutional neural network;

generating a loss function based on the plurality of masks;

iteratively back propagating the loss function to tune parameters of the convolutional neural network;

predicting a classification label for an input image based on the convolutional neural network; and generating a multi-dimensional visualization associated with the classification label for the input image.

9. The method of claim 8, further comprising matching a size of a mask from the plurality of masks with a size of a convolutional feature map from the convolutional feature maps.

10. The method of claim 8, further comprising matching a size of a mask from the plurality of masks with a size of a convolutional feature map from the convolutional feature maps based on a max pooling process.

11. The method of claim 8, wherein the generating the loss function comprises employing the decoder to generate the localization map.

12. The method of claim 8, wherein the generating the loss function comprises generating the loss function based on a probability for a class associated with the plurality of masks.

13. A computer readable storage device comprising instructions that, in response to execution, cause a system comprising a processor to perform operations that employ masks and decoders for improved performance, comprising:

receiving a plurality of images associated with a plurality of patients from at least one imaging device;

receiving a plurality of masks from a plurality of objects, wherein each image comprises at least one mask associating an object of interest with a corresponding class label;

training a convolutional neural network based on the plurality of images and the plurality of masks, wherein the convolutional neural network comprises a decoder consisting of at least one up-sampling layer and at least one convolutional layer, a pretrained classifier network that outputs convolutional feature maps, and a classification/localization network that outputs corresponding scoring maps, wherein the decoder is a set of decoders;

determining a number of decoders in the set of decoders during the training of the convolutional neural network;

generating a loss function based on the plurality of masks;

iteratively back propagating the loss function to tune parameters of the convolutional neural network;

predicting a classification label for an input image based on the convolutional neural network; and generating a multi-dimensional visualization associated with the classification label for the input image.

14. The computer readable storage device of claim 13, wherein the generating the loss function comprises employing the set of decoders to generate the localization map.

15. The computer readable storage device of claim 13, wherein the generating the loss function comprises generating the loss function based on a probability for a class associated with the plurality of masks.

* * * * *